United States Patent [19]

Blessinger

[11] Patent Number: 4,920,971

[45] Date of Patent: May 1, 1990

[54] PNEUMATIC VEIN INFLATION DEVICE

[76] Inventor: Martin W. Blessinger, 95 Sagamore Dr., Syosset, N.Y. 11791

[21] Appl. No.: 281,627

[22] Filed: Dec. 9, 1988

[51] Int. Cl.⁵ ............................................. A61B 5/022
[52] U.S. Cl. .................................... 128/679; 128/686; 606/202
[58] Field of Search ................ 128/327, 672, 677–686

[56] References Cited

U.S. PATENT DOCUMENTS

| 3,527,204 | 9/1970 | Lem | 128/686 X |
| 3,633,567 | 1/1972 | Sarnoff | 128/686 |
| 4,210,154 | 7/1980 | Klein | 128/686 X |
| 4,635,635 | 1/1987 | Robinette-Lehman | 128/327 |
| 4,637,394 | 1/1987 | Racz et al. | 128/327 |

Primary Examiner—Angela D. Sykes
Attorney, Agent, or Firm—Michael I. Kroll

[57] ABSTRACT

In one particularly desirable form of the invention, the pneumatic vein inflation device for assisting in a medical testing and/or treatment procedure comprises a hard cylindrical tube, two inflatable ring-shaped bladders positioned in succession axially inside the hard cylindrical tube, an elastic jacket enclosing the inflatable bladders and the cylindrical tube holding the inflatable bladders in place and a means for pressurization and relief including a hand powered air pump and associated relief valve connected to a distribution valve which in turn is connected to one or the other inflatable bladder and a pressure gauge. Other forms of the instant invention can have various numbers of inflatable bladders.

4 Claims, 1 Drawing Sheet

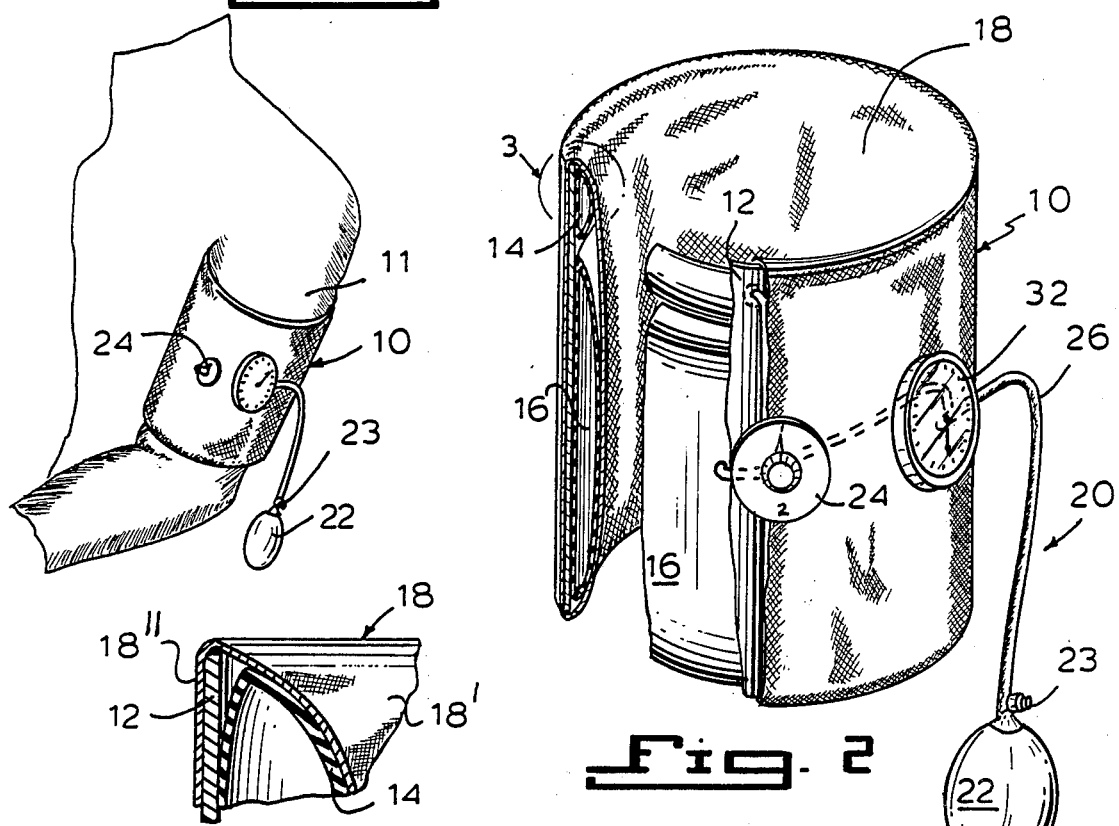
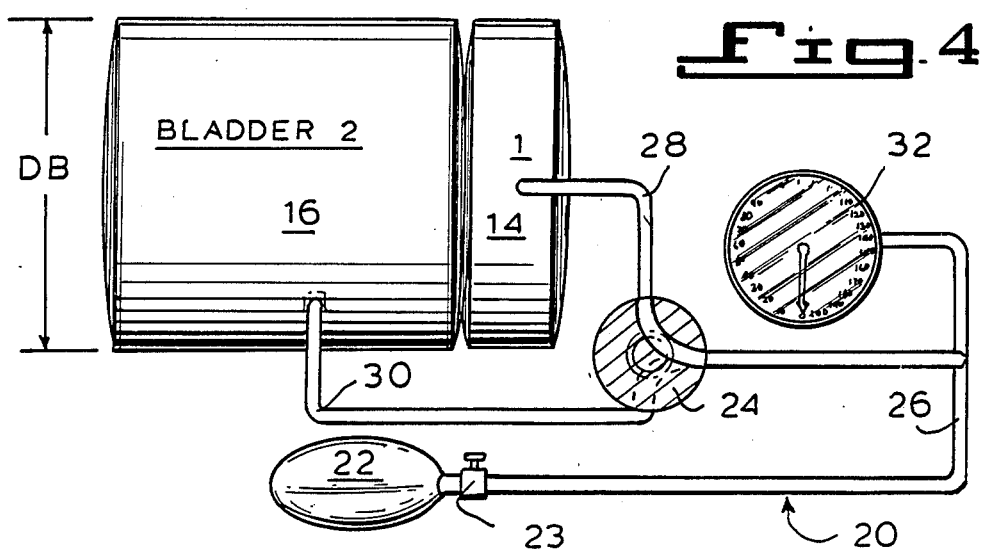

PNEUMATIC VEIN INFLATION DEVICE

THE FIELD OF THE INVENTION

The instant invention relates to medical equipment for a treatment and/or testing procedure and, more particularly, to a medical device which facilitates the insertion of an intravenous needle.

THE BACKGROUND OF THE INVENTION

Intravenous feeding like several medical procedures requires insertion of a hollow needle in a vein to provide needed nutrients with medication and/or vitamins and is often initiated because the patient may be unconscious and/or is in cardiac arrest. A blood transfusion is another example of a medical procedure which requires insertion of a hollow needle in a vein. In many individuals a vein in the arm can be found easily for these purposes and can be inflated by applying manual pressure to the arm, but in a significant number of individuals, especially those in severe shock or cardiac arrest where their circulatory system may be in vascular collapse, the insertion of an intravenous needle will be significantly more difficult and time-consuming.

The measurement of blood pressure by a sphygmomanometer takes place by restricting the flow of blood using a pneumatic device comprising a rubber bladder covered by a long cloth sleeve and a rubber bulb connected to the bladder which can inflate it. This pneumatic device which is wrapped around the arm like a cuff during the measurement of blood pressure, restricts the flow of blood in the arm without injuring the individual.

It is an object of the instant invention to provide a pneumatic vein inflation device which holds back the flow of blood in a vein in an extremity, especially in an arm, and acts to inflate the vein for a medical testing and/or treatment procedure, by transposing a volume of blood from the upper arm to the lower arm.

It is also an object of the invention to provide a pneumatic vein inflation device which helps inflate a vein in an extremity, especially an arm, of an individual to initiate intravenous feeding of the individual.

It is another object of the invention to provide a pneumatic vein inflation device which helps inflate a vein in an extremity, especially an arm, of an individual to facilitate insertion of a hollow needle in the vein to draw blood or perform a blood transfusion.

It is a general object of the invention to provide a device which facilitates otherwise time-consuming and difficult intravenous procedures for individuals whose veins are difficult to find, toughened by old age or in vascular collapse.

THE SUMMARY OF THE INVENTION

According to the invention, the pneumatic vein inflation device for assisting in a medical testing and/or treatment procedure comprises a hard cylindrical tube, advantageously two inflatable ring-shaped bladders positioned in succession axially inside the hard cylindrical tube having a diameter somewhat less than the inner diameter of the hard cylindrical tube and a means for pressurization and relief of the inflatable bladders to and from a predetermined pressure and for distributing pressure between the inflatable bladders. The inflatable bladders are of such size that an extremity of an individual undergoing the medical testing and treatment procedure fits therein.

In one advantageous embodiment of the invention, there are two inflatable bladders one of which is significantly larger than the other, and the means for pressurization and relief comprises a hand-powered air pump and associated relief valve connected by a first air hose section to a three-way distribution valve, which in turn is connected by a second air hose section to the first smaller inflatable bladder, and by a third air hose section to the other larger inflatable bladder and a pressure gauge connected to the first air hose section.

An elastic jacket surrounding both inflatable bladders and the cylindrical tube can be provided to hold the inflatable bladders in place in the cylindrical tube. It can comprise an outer tubular sheath of substantially the same height as the inner tubular sheath, the opposite ends of the inner tubular sheath being attached to the corresponding opposite ends of the outer tubular sheath to form the jacket. The inner and outer sheath may be made of nylon. Advantageously, the inflatable bladders are made of an elastic material, for example rubber.

When there is difficulty finding a vein for insertion for a hollow needle for intravenous feeding or for another procedure, the pneumatic vein inflation device is slipped on the upper arm and the first smaller advantageously donut-like inflatable bladder is pressurized to a predetermined safe pressure with the hand pump while observing the pressure gauge so that the flow of blood in the vein is stopped temporarily. Then the distribution valve is turned, isolating the first inflatable bladder, and then the second longer bladder is pressurized until the vein in question is observable. Thus with the invention, a satisfactory intravenous feeding is possible.

BRIEF DESCRIPTION OF THE DRAWING FIGURES

FIG. 1 is a schematic perspective view showing a pneumatic vein inflation device according to the instant invention in position on the arm of an individual requiring an intravenous medical procedure.

FIG. 2 is a partially perspective, partially cutaway cross sectional view of the vein inflation device of FIG. 1.

FIG. 3 is a detailed cross sectional view of the portion of the vein inflation device of FIG. 1 indicated with the dot-dashed circle 3 of FIG. 2.

FIG. 4 is a diagrammatic view of the vein inflation device of FIG. 1 showing a means for pressurizing its inflatable bladders with a pressure gauge, air pump, air hose and valves.

DETAILED DESCRIPTION OF THE INVENTION

The embodiment of the pneumatic vein inflation device 10 shown in the drawing comprises a hard cylindrical tube 12, two internal inflatable ring-shaped bladders 14,16 positioned in succession axially inside the hard cylindrical tube 12, having a diameter DB less than the inner diameter of the hard cylindrical tube so that they just fit inside it, and a means for pressurization and relief 20 for pressurizing (and depressurizing) the inflatable bladders 14,16 to a predetermined pressure and for distributing pressure between the bladders.

Both internal inflatable bladders 14 and 16 have the same diameter DB and are made of rubber or some other inflatable material, but the first inflatable bladder 14 is considerably smaller in height than the other second inflatable bladder 16. The inflatable bladders 14 and 16 are held in position in the hard cylindrical tube 12 by an elastic jacket 18, advantageously made of nylon, which comprises an inner tubular sheath 18' and an outer tubular sheath 18" of substantially the same height attached to each other at opposite ends of the vein inflation device 10 to form an envelope enclosing the hard cylindrical tube 12 and the inflatable bladders 14 and 16. The size and elasticity of the inner tubular sheath 18' and the outer tubular sheath 18" are such that the inflatable bladders 14 and 16 are held in position when not inflated. This expandable jacket 18 helps keep the inflatable bladders 14,16 in position when they are being inflated.

The means for pressurization and relief 20 includes a hand powered air pump 22 and associate relief valve 23 for release of pressure similar to that used in the conventional blood pressure measuring device. This hand powered air pump 22 is connected to a distribution valve 24, which is essentially a three-way valve, by a first air hose section 26. The three-way distribution valve 24 is also connected on its other side to both inflatable bladders 14,16 by a second and third section of air hose 28,30. A pressure gauge 32 is connected to the first air hose section 26 between the distribution valve 24 and the air pump 22 and measures total pressure in the inflatable bladder 14 or 16 which the distribution valve 24 selects. This pressure gauge or pneumatic meter 32 is a conventional pressure measuring device.

The operation of this embodiment of the pneumatic vein inflation device according to the invention is as follows:

The vein inflation device 10 is slid on the upper arm 11 in the position shown in FIG. 1 with the inflatable bladders 14, 16 deflated. Then the air pump 22 is squeezed repeatedly with the relief valve 23 closed and the distribution valve 24 set so that the first donut-shaped inflatable bladder 14 is inflated to a predetermined pressure which can be determined from the pressure gauge 32. When that pressure is reached, the first inflatable bladder 14 is isolated by resetting the distribution valve 24. At this point the flow of blood back to the torso from the upper arm 11 should be stopped or greatly reduced (by appropriate selection of the final pressure). Then the larger inflatable bladder 16 is inflated to a point where the vein in the arm 11 is suitable for easy initiation of the desired intravenous procedure. Upon completion of that procedure, the device is deflated by opening the relief valve 23, and the distribution valve 24 selects the appropriate bladders 14, 16 in reverse order to that used in inflation.

In other embodiments the number of bladders used in the invention may be varied from one to several within the scope of the invention.

No specific dimensions for the inflatable bladders, the elastic jacket or the hard cylindrical tube have been provided because of the wide variation between individuals due to age, weight and/or gender.

LIST OF REFERENCE NUMBERS 10 pneumatic vein inflation device(the invention)
11 arm
12 hard cylindrical tube
14 first donut-shaped inflatable bladder
16 second inflatable bladder
18 elastic jacket
18' inner tubular sheath
18" outer tubular sheath
20 means for pressurization and relief
22 hand powered air pump
23 relief valve
24 distribution valve
26 first air hose section
28 second air hose section
30 third air hose section
32 pressure gauge
DB diameter of the inflatable bladders It will be understood that each of the elements described above, or two or more together, may also find a useful application in other devices differing from the type of device described above.

The invention is not intended to be limited to the details provided above and it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention.

What is claimed is new and what is desired to be protected by Letters Patent is set forth in the following claims:

1. A pneumatic vein inflation device for assisting in a medical testing and/or treatment procedure comprising:
   (a) a fastenerless hard inflexible cylindrical tube;
   (b) two internal inflatable cylindrical ring-shaped bladders positioned in succession axially inside said fastenerless hard inflexible cylindrical tube having a diameter substantially less than the inner diameter of said fastenerless hard inflexible cylindrical tube and each of said inflatable cylindrical ring shaped bladders being used successively during any and all given usages;
   (c) means for pressurization and relief of said inflatable cylindrical ring shaped bladders to and from a predetermined pressure that will be customized for each usage, and for distributing said pressure between said inflatable cylindrical ring shaped bladders, said inflatable cylindrical ring shaped bladders being of a size such that an extremity of an individual undergoing said medical testing and treatment procedure fits therein;
   (d) said means for pressurization and relief comprises a hand powered air pump and a single associated relief valve connected by a first air hose section to a three way distribution valve which in turn is connected by a second air hose section to one of said inflatable cylindrical ring shaped bladders and by a third air hose section to the other of said inflatable cylindrical ring shaped bladders, and a pressure gauge connected to said first air hose section; and
   (e) an elastic jacket surrounding said inflatable cylindrical ring shaped bladders and said fastenerless hard inflexible cylindrical tube comprising an inner tubular sheath and an outer tubular sheath of substantially the same height as said inner tubular sheath, the opposite ends of said inner tubular sheath being homogeneously attached to the corresponding opposite ends of said outer tubular sheath to form said elastic jacket which holds said inflatable cylindrical ring shaped bladders in place in said fastenerless hard inflexible cylindrical tube.

2. A pneumatic vein inflation device according to claim 1 in which said means for pressurization and relief comprises a hand powered air pump and said single associated relief valve for release of pressure and being connectable by flexible air hose section with either of said inflatable cylindrical ring shaped bladders according to choice.

3. A pneumatic vein inflation device according to claim 2 in which said means for pressurization and relief further comprises a pressure gauge so that said inflatable cylindrical ring-shaped bladders may be inflated to a predetermined pressure that will be customized for each usage.

4. A pneumatic inflation device for assisting in a medical testing and/or treatment procedure comprising:
 (a) a fastenerless hard inflexible cylindrical tube;
 (b) at least two internal inflatable cylindrical ring-shaped bladders positioned in succession axially inside said fastenerless hard inflexible cylindrical tube having a diameter less than the inner diameter of said fastenerless hard inflexible cylindrical tube;
 (c) an elastic jacket comprising an inner tubular sheath and an outer tubular sheath attached to said inner tubular sheath at opposing ends surrounding said inflatable cylindrical ring-shaped bladders and said fastenerless hard inflexible cylindrical tube holding said inflatable cylindrical ring-shaped bladders in said fastenerless hard inflexible cylindrical tube; and
 (d) means for pressurization and relief of said inflatable cylindrical ring-shaped bladders haivng a hand powered air pump and a single associated relief valve connected by a first air hose section to a three-way distribution valve which in turn is connected by a second air hose section to one of said inflatable cylindrical ring like bladders and by a third air hose section to another of said inflatable cylindrical ring like bladders and a pressure gauge connected to said first air hose section.

* * * * *